US012161405B2

United States Patent
Di Sessa et al.

(10) Patent No.: US 12,161,405 B2
(45) Date of Patent: Dec. 10, 2024

(54) MEDICAL DEVICES WITH USER AND PATIENT FEEDBACK

(71) Applicant: Azena Medical, LLC, Walnut Creek, CA (US)

(72) Inventors: Alexandre B. Di Sessa, Walnut Creek, CA (US); Jacob Manshiro Abe, San Jose, CA (US)

(73) Assignee: Azena Medical, LLC, Walnut Creek, CA (US)

( * ) Notice: Subject to any disclaimer, the term of this patent is extended or adjusted under 35 U.S.C. 154(b) by 340 days.

(21) Appl. No.: 17/560,911

(22) Filed: Dec. 23, 2021

(65) Prior Publication Data
US 2023/0200905 A1   Jun. 29, 2023

(51) Int. Cl.
*A61B 18/20* (2006.01)
*A61B 18/00* (2006.01)

(52) U.S. Cl.
CPC .... *A61B 18/20* (2013.01); *A61B 2018/00577* (2013.01); *A61B 2018/00642* (2013.01); *A61B 2018/0091* (2013.01)

(58) Field of Classification Search
None
See application file for complete search history.

(56) References Cited

U.S. PATENT DOCUMENTS

| | | | |
|---|---|---|---|
| 2009/0319008 A1* | 12/2009 | Mayer | A61N 5/0624 607/90 |
| 2012/0116364 A1* | 5/2012 | Houser | A61B 46/10 606/1 |
| 2013/0169412 A1* | 7/2013 | Roth | H01H 3/14 340/6.1 |
| 2015/0112411 A1* | 4/2015 | Beckman | A61N 5/0616 607/90 |
| 2018/0369609 A1* | 12/2018 | Wilder Smith | A61B 17/320068 |

* cited by examiner

*Primary Examiner* — Ankit D Tejani
(74) *Attorney, Agent, or Firm* — Carr & Ferrell LLP (57) ABSTRACT

Medical ablation devices with user and patient feedback are disclosed herein. An example system a first haptic feedback element, a handpiece that is configured to deliver therapeutic light, a foot pedal that is configured to receive user input to control the therapeutic light, and a controller including a processor and memory, the processor executing instructions stored in the memory to: determine a selection of an operating mode of a plurality of operating modes, the operating mode having a haptic feedback feature; receive the user input from a user; and cause the first haptic feedback element to generate haptic feedback based on the user input.

23 Claims, 8 Drawing Sheets

MEDICAL DEVICES WITH USER AND PATIENT FEEDBACK

CROSS-REFERENCE TO RELATED APPLICATIONS

N/A

TECHNICAL FIELD

This disclosure pertains to medical devices, and more specifically, but not by way of limitation, to medical devices that provide feedback to both users and patients. This feedback can include tactile feedback such as haptic vibration, along with other non-tactile types of feedback.

SUMMARY

According to some embodiments, the present disclosure is directed to a device that includes a first haptic feedback element; a handpiece that is configured to deliver therapeutic light; a foot pedal that is configured to receive user input to control the therapeutic light; and a controller comprising a processor and memory, the processor executing instructions stored in the memory to: determine a selection of an operating mode of a plurality of operating modes, the operating mode having a haptic feedback feature; receive the user input from a user; and cause the first haptic feedback element to generate haptic feedback based on the user input.

According to some embodiments, the present disclosure is directed to a device comprising a handpiece that is configured to deliver laser light, the handpiece comprising a first haptic feedback element; a foot pedal that is configured to receive input from a user for operating the handpiece, the foot pedal comprising a second haptic feedback element; and a controller comprising a processor and memory, the processor executing instructions stored in the memory to activate the first haptic feedback element and the second haptic feedback element only when the user has selected a photobiomodulation mode of the device.

According to some embodiments, the present disclosure is directed to a method comprising determining when a user has selected a photo-biomodulation procedure mode for a medical laser device; receiving input from the user via a handpiece or foot pedal; and causing a first haptic feedback element in the handpiece to generate haptic feedback based on the input, when laser light is being delivered by the handpiece.

BRIEF DESCRIPTION OF DRAWINGS

Exemplary embodiments are illustrated by way of example and not limitation in the figures of the accompanying drawings, in which like references indicate similar elements.

DETAILED DESCRIPTION OF EXAMPLE EMBODIMENTS

Overview

This disclosure pertains to medical devices, and more specifically, but not by way of limitation, to medical devices that provide feedback to both users and patients. This feedback can include tactile feedback such as haptic vibration, along with other non-tactile types of feedback.

Laser emitting devices, such as ablation systems work by producing laser light through tissue absorption. This laser light can be transmitted through a fiber optic or other medium where it is directed at a biological substrate, such as a soft or hard tissue of a patient. It will be understood that the present disclosure pertains not only to laser light devices, but also more generally to devices that can use therapeutic light generated by a laser, a light emitting diode (LED), or other element that can produce a therapeutic light. Moreover, therapeutic light can include any wavelength of light that can be used in a medical procedure, such as photobiomodulation, ablation, sterilization, cleaning, and so forth—just to name a few.

When working with laser light during ablation procedures, it is often difficult, if not impossible, to determine when the laser light is being emitted due to environmental noises. This can be exacerbated when the laser light selected is not in a visible wavelength, or when other factors are present. Furthermore, some individuals may have reduced quality eyesight or may be colorblind, reducing their ability to see the laser light, even if it is colored and/or visible. When wearing laser safety eyewear, the infrared (IR) light is completely blocked and the only way to see laser function is via the aiming light or sound.

Thus, in some instances, it is advantageous to provide a user of the medical device with feedback that is not entirely visual. In some embodiments, this can include providing haptic feedback that provides the user with a gentle vibrational pulse. In some embodiments, the haptic feedback is available when the user selects a specific operating mode for the device. For example, haptic feedback may be activated on the device when the user has selected photobiomodulation. In one embodiment, each operating mode of the laser can have its own unique haptic vibrational pattern. In some instances, a magnitude of the haptic feedback can be selectively adjusted according to a magnitude of a power setting for the laser. For example, the vibration setting for the haptic feedback is set at a first magnitude when the user has selected a low power setting for the laser. The vibration setting for the haptic feedback is set at a second magnitude when the user has selected a higher power setting for the laser. Thus, the magnitude of the vibration setting for the haptic feedback can increase and/or decrease proportionally to the power setting.

In some embodiments, different intensities for the haptic feedback can be selected or modulated based on a procedure countdown. For instance, during a procedure that takes 30 seconds, the haptic feedback initiates at low vibration and increases during the last five seconds to alert the user it is reaching the end of the 30 second treatment. For example, the haptic feedback can start at ten seconds to procedure end and increase in intensity over time increments of two seconds, reaching maximum intensity in the last five seconds. While this example has been given, it is not intended to be limiting. These and other advantages will be described in greater detail herein.

Example Embodiments

Figure 1:
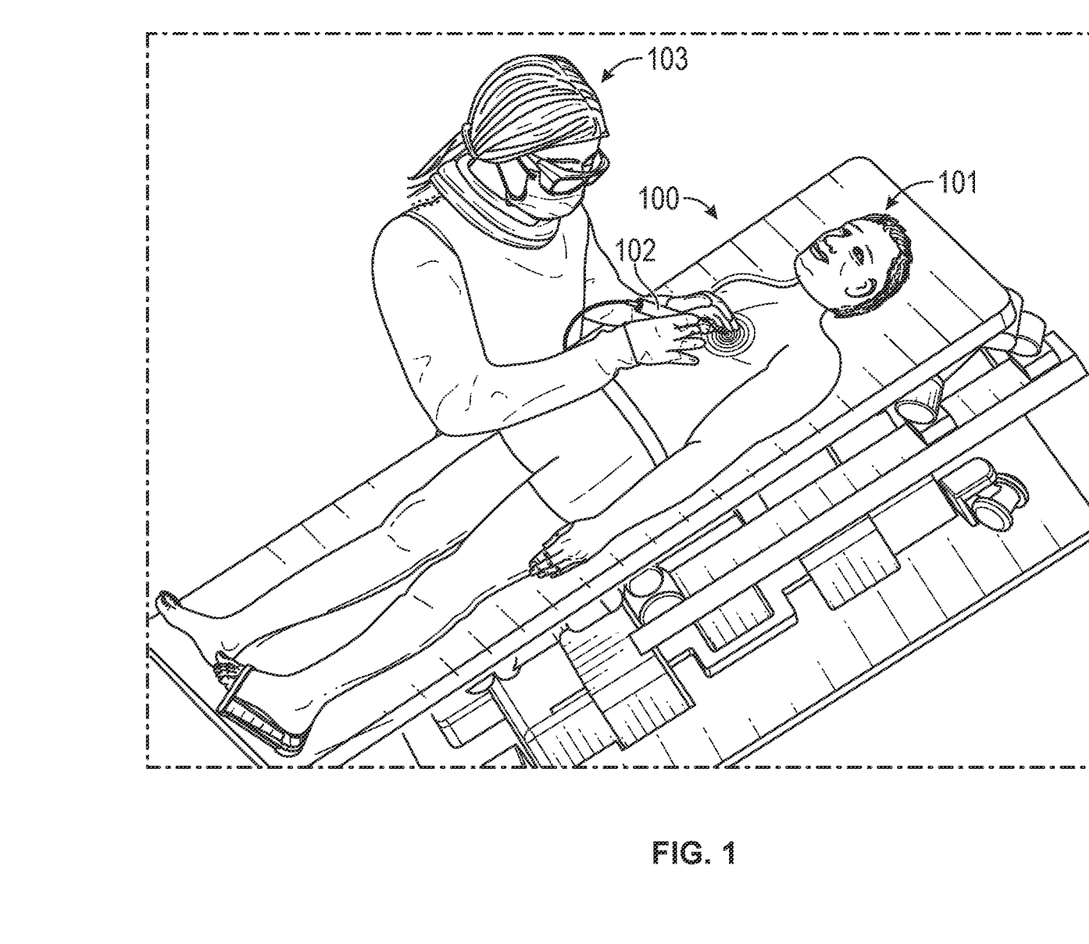
FIG. 1 is an example environment where aspects of the present disclosure can be implemented for use.
Figure 2A:
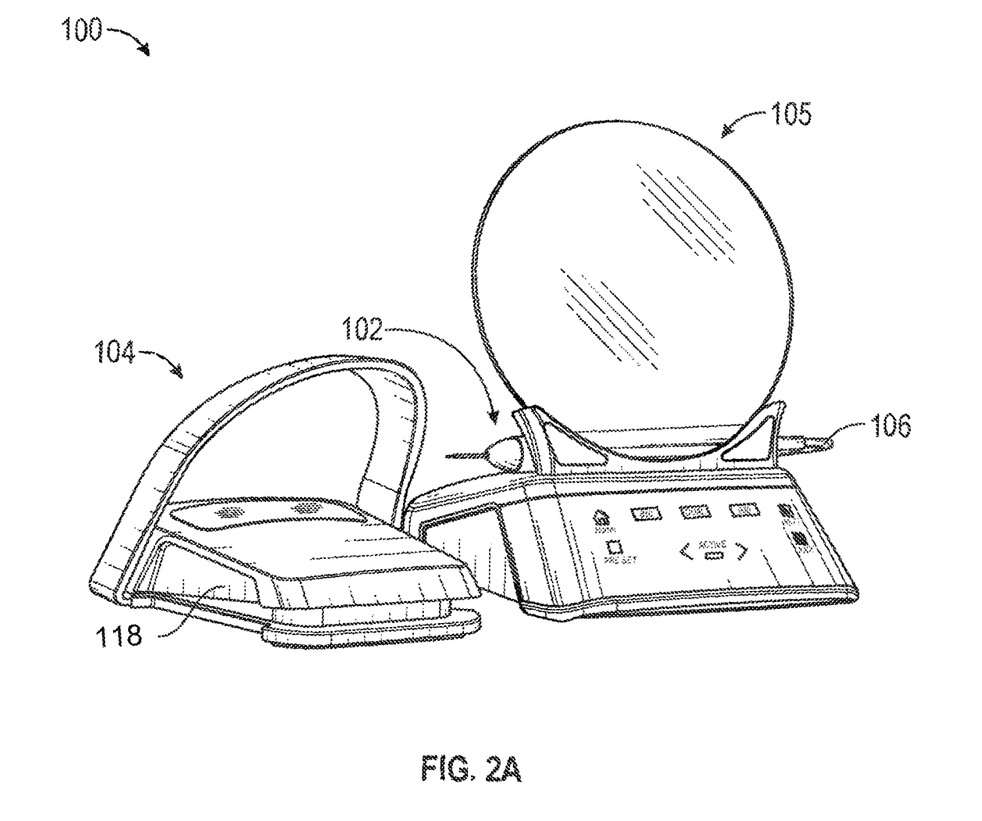
FIG. 2A is a perspective view of an example device that provides haptic feedback.

Referring now to FIG. 1, which illustrate an example architecture where aspects of the present disclosure are implemented. An example laser device 100 can be used to process the skin of a patient 101. The device 100 can provide a user 103 with haptic feedback when the device 100 is delivering laser light to the outside skin, intra oral soft or hard tissue of the patient 101. In this example, a handpiece 102 of the device 100 is illustrated as providing haptic feedback to the user 103. An example foot piece of the device 100 is illustrated in FIG. 2.

Figure 2B:
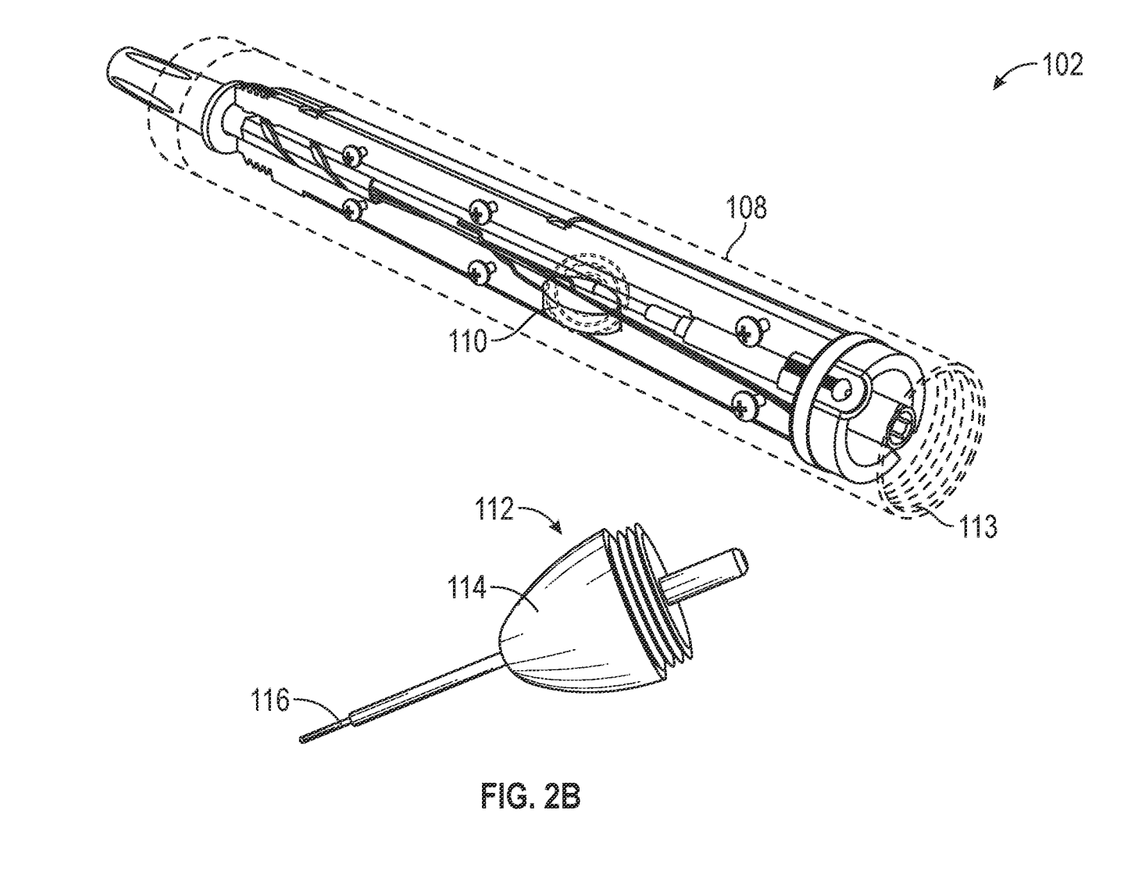
FIG. 2B is a cross-sectional view of an example handpiece, illustrating a haptic motor.
Figure 2C:
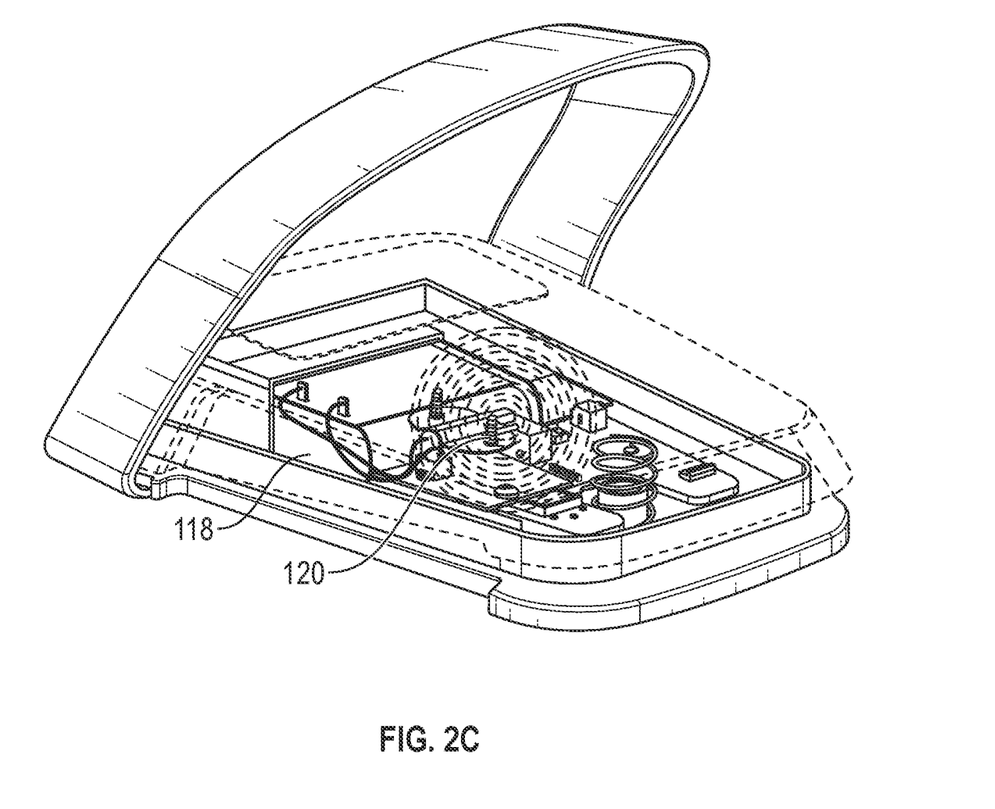
FIG. 2C is a cross-sectional view of an example foot pedal, illustrating a haptic motor.
Figure 3:
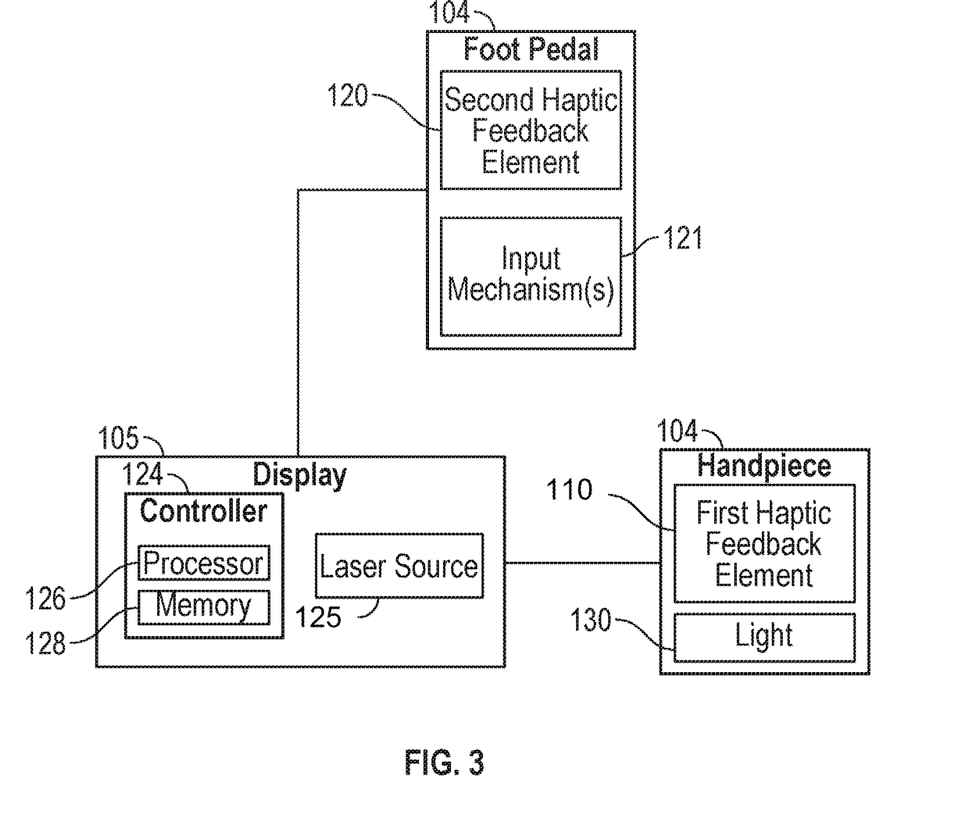
FIG. 3 is a schematic diagram of a portion of the example laser device of FIG. 2A.

Referring now to FIGS. 1-3 collectively, the device 100 is a laser system that can be used to ablate, photobiomodulate, and/or otherwise process biological tissue with laser light. In one example, the device 100 can comprise the handpiece 102, the foot pedal 104, and a display 105. The handpiece 102 and display 105 can be configured to communicate with one another over a wired or wireless connection. One example wireless connection can include a short-range wireless connection such as BLUETOOTH. The handpiece 102 can also be coupled to the display 105 through a cable 106 that enshrouds a fiber optic or other light-transmissive filament. When a cable is used, communication between the handpiece 102 and display 105 can occur through the cable 106. The foot pedal can also be coupled to the display 105 and/or handpiece 102 via a wired or wireless connection.

The user can turn on the device 100 through the use of foot pedal 104 or the display 105. In general, the foot pedal 104 allows the user to control the functions of the device 100, and in turn, the functions of the handpiece 102 through foot taps or other input. These functionalities can also be controlled through the display 105, which provides touch-screen elements and/or physical actuators.

Regardless of whether the user chooses to use the foot pedal 104 or handpiece 102, the user can select a mode of operation of the device 100, such as ablation, photobiomodulation, or any other operating mode. The user can also select other operating parameters such as power level.

In general, the handpiece 102 is configured to deliver laser light to a target biological substrate, such as skin. The handpiece 102 includes a housing 108, a first haptic feedback element 110, and a disposable tip 112. The disposable tip 112 can include an illuminable cap 114 and a fiber optic element 116 that can be attached to a terminal end 113 of the housing 108. The first haptic feedback element 110 can comprise a haptic motor that is mounted within the housing 108 at a location away from the disposable tip 112 that is near or at where a user will place their hand to hold the handpiece 102. The shape of the handpiece 102 allows the user to hold the handpiece 102 like a writing instrument. Thus, the location of the first haptic feedback element 110 may be selected to ensure that it is close to the area where a user would grip or hold the handpiece 102.

The foot pedal 104 can also comprise a housing 118, a second haptic feedback element 120, and one or more input mechanisms 121 (see FIG. 3). Generally, the foot pedal 104 is configured to receive user input through the one or more input mechanisms 121 to control the laser light emitted by the handpiece 102. For example, the one or more input mechanisms 121 could include buttons, switches, or other sensors that can receive input from a foot of a user to activate one or more features of the device 100. The second haptic feedback element 120 can include a haptic motor that is located near a position on the foot pedal 104 where the user's foot is likely to contact the housing 118 when the user has placed their foot into the foot pedal 104.

The display 105 can comprise a controller 124 and a laser source 125. The controller 124 comprises a processor 126 and memory 128. The processor 126 executes instructions stored in memory 128 to provide one or more of the functionalities disclosed herein. When referring to actions performed by the controller 124, this will be understood to include execution of instructions by the processor 126.

The controller 124 can be configured to determine what mode of operation has been selected by the user. For example, the controller 124 can determine when the user has selected ablation or photobiomodulation modes. When the user has selected a photobiomodulation mode, the controller 124 can activate a haptic feedback mode. That is, haptic feedback can be linked to the photobiomodulation mode, such that haptic feedback is only available when the user has selected the photobiomodulation mode. In other embodiments, haptic feedback may be allowed for other modes. Thus, the controller 124 can determine a selection of an operating mode of a plurality of operating modes, the operating mode having a haptic feedback feature. In some instances, the user can switch operating modes using the foot pedal 104.

Once the operating mode has been selected, the controller 124 can determine when the user provides input to the foot pedal 104. For example, when the user presses on the foot pedal 104 with their foot, a pressure sensor in the foot pedal housing can detect this pressure and activate the laser source 125. While a pressure sensor is disclosed, any other means for detecting foot pressure can be used.

Laser light is generated by the laser source 125 and transmitted through the cable 106 to the disposable tip and the fiber optic element 116. When the photobiomodulation mode and the controller 124 detects activation of the laser source 125, the controller 124 activates the first haptic feedback element 110. In some instances, haptic feedback propagates to the tip of the handpiece, allowing the haptic feedback to be felt by a skin of a patient.

In one example, the first haptic feedback element 110 vibrates as the user's foot presses on the foot pedal 104 to activate the laser source 125. In some embodiments, the controller 124 can pulse the first haptic feedback element 110 rather than using continuous vibration. In various embodiments, the controller 124 can also activate the second haptic feedback element 120 to give the user a second type of haptic feedback to their foot.

As noted above, the user can select a power level for the laser source 125. The user can select this power level at the display 105 or through use of the foot pedal 104. The controller 124 can selectively adjust a magnitude of the haptic feedback produced by either/both of the first haptic feedback element 110 and the second haptic feedback element 120 based on a power level or setting of the laser source 125.

For example, a vibration setting for the first haptic feedback element 110 is set at a first magnitude when the user has selected a first power setting for the laser. The vibration setting for the first haptic feedback element 110 is set at a second magnitude when the user has selected a higher power setting for the laser. Thus, the magnitude of the vibration setting for the first haptic feedback element 110 can increase and/or decrease proportionally to the power setting. The same selective adjustment can occur with respect to the second haptic feedback element 120. In sum, the controller 124 can selectively and proportionally adjust a magnitude of the haptic feedback based on the power setting. Thus, as the power level increases, the haptic feedback gets stronger. In other embodiments, the first haptic feedback element 110 and/or second haptic feedback element 120 can be pulsed faster or slower based on the power setting. The feedback elements can be pulsed slower at lower power levels and faster at higher power levels. Again, this selective pulsing can be proportional to the power setting.

In various embodiments, the vibration pattern for the first haptic feedback element 110 and the second haptic feedback element 120 can be independently controlled. For example, the controller 124 can be configured to pulse the first haptic feedback element 110 according to a first pulse pattern. The controller 124 can pulse the second haptic feedback element 120 according to a second pulse pattern. The first pulse pattern is different from the second pulse pattern in some instances. For example, the first pulse pattern could be intermittent vibration and the second pulse pattern may be continuous.

In yet other examples, the controller 124 can activate the first and/or second haptic feedback element(s) in accordance with a countdown process. For instance, during a procedure that takes 30 seconds, the haptic feedback initiates at low vibration and increases during the ten five seconds to alert the user it is reaching the end of a one-minute treatment. For example, the haptic feedback can start at thirty seconds to procedure end and increase in intensity over time increments of five or ten seconds, reaching maximum intensity in the last five seconds. Again, while this example has been given, it is not intended to be limiting. A light used to illuminate a tip of the laser device, as discussed below, can also be controlled to indicate a countdown. Using the example above, the controller 124 can activate a light on the device at thirty seconds to procedure end and blink the light in the last five seconds to inform the user that the procedure is reaching it end. These features can be used to prevent the user from over treating the target tissue of the patient.

As noted above, the disposable tip 112 can include a light 130 that can be illuminated by the controller 124. That is, in response to user input, such as foot pressure to the foot pedal 104, the controller 124 can activate the light 130. This provides the user with a second type of feedback that is visual in nature. While the fiber optic element 116 of the disposable tip 112 emits laser light that in some cases can be seen, the light emitted may be difficult to see due to its size. The light 130, when activated, illuminates the illuminable cap 114.

In various embodiments, the controller 124 can activate the light 130 in conjunction with either or both of the first haptic feedback element 110 and the second haptic feedback element 120. In some instances, when the controller 124 is pulsing the first haptic feedback element 110 and/or the second haptic feedback element 120, the controller 124 can pulse the light 130 correspondingly.

Figure 4:
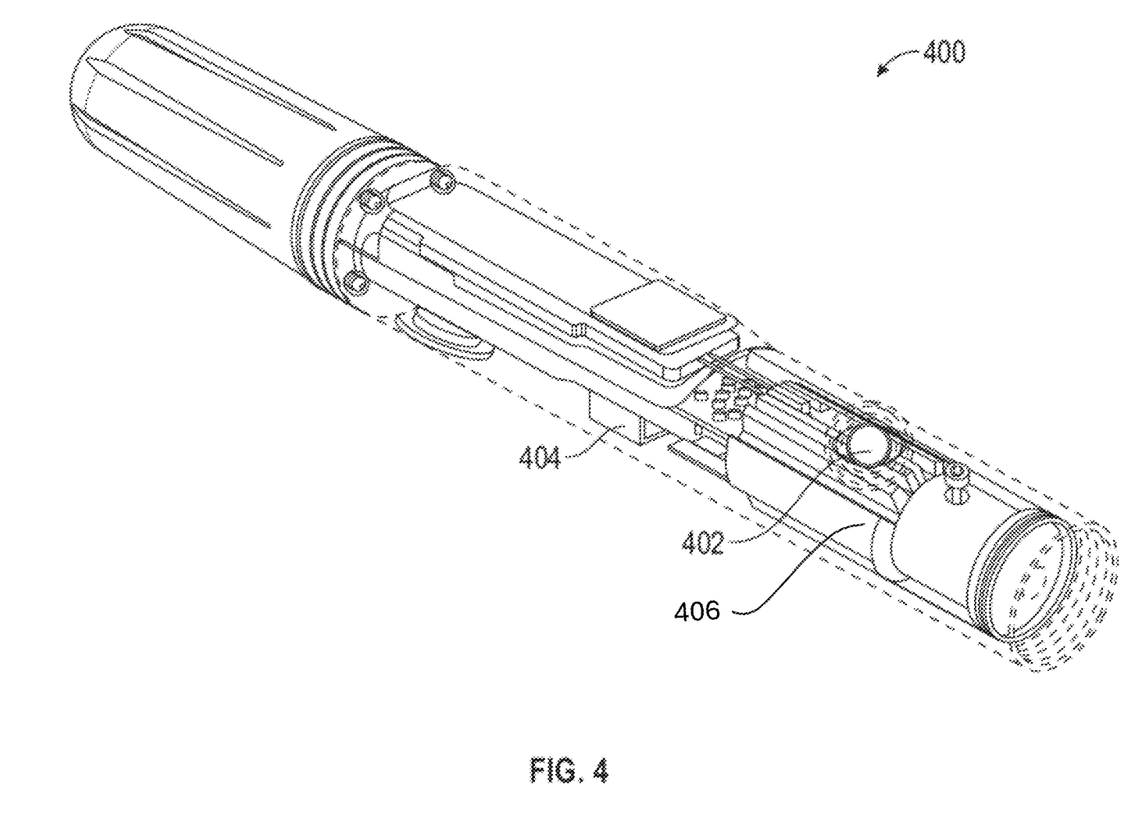
FIG. 4 is a perspective view of another example device that provides haptic feedback.

FIG. 4 is a perspective view of another example laser device 400 that is self-contained. That is, in the embodiments described above, a controller was embedded in a foot pedal. In the embodiment of FIG. 4, the device 400 is self-contained, requiring no foot pedal. It will be understood that a wireless foot pedal can be included in some embodiments. The device 400 can include a haptic element, such as a haptic motor 402 and a laser source 406 that is located inside a housing 404. Again, the user can hold the device 400 like a writing instrument. Thus, the haptic motor 402 can be located near where a user's fingers will grip the device 400.

Figure 5:
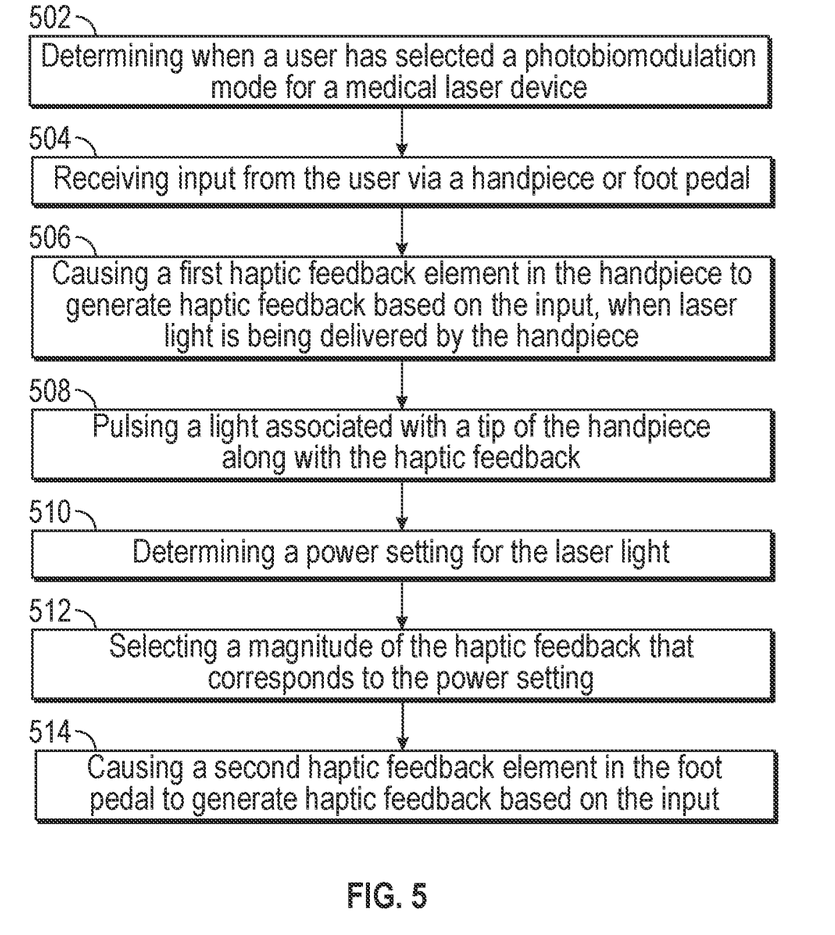
FIG. 5 is a flowchart of an example method of the present disclosure.

FIG. 5 is a flowchart of an example method of the present disclosure. The method can include a step 502 of determining when a user has selected a photobiomodulation mode for a medical laser device. For example, the user can select the photobiomodulation mode through a display or by using a foot pedal. Next, the method includes a step 504 of receiving input from the user via a handpiece or foot pedal. The user could press the foot pedal to activate a laser source as an example input. The handpiece could include a button or switch that the user employs to activate the laser source. The method can also include a step 506 of causing a first haptic feedback element in the handpiece to generate haptic feedback based on the input, when laser light is being delivered by the handpiece.

The method can also include a step 508 of pulsing a light associated with a tip of the handpiece along with the haptic feedback. In some embodiments, the method can include a step 510 of determining a power setting for the laser light, as well as a step 512 of selecting a magnitude of the haptic feedback that corresponds to the power setting. In one or more embodiments, the method can include a step 514 of causing a second haptic feedback element in the foot pedal to generate haptic feedback based on the input. It will be understood that the order of operations disclosed above is not intended to be limiting and that elements in the flow chart can be rearranged as would be appreciated by one of ordinary skill in the art.

Figure 6:
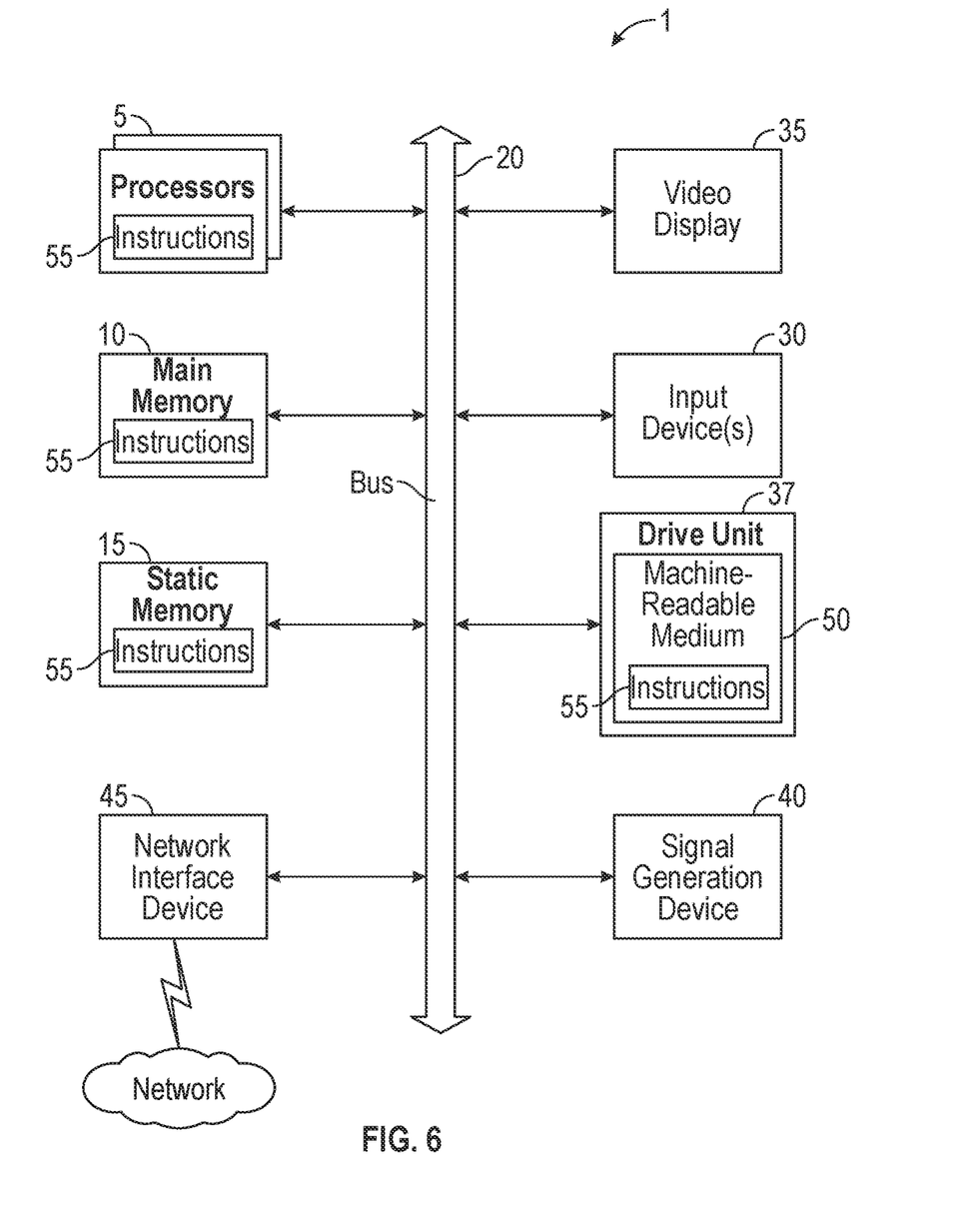
FIG. 6 is a simplified block diagram of a computing system, in accordance with some embodiments.

FIG. 6 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as a Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alphanumeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The drive unit 37 includes a computer or machine-readable medium 50 on which is stored one or more sets of instructions and data structures (e.g., instructions 55)

embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In this description, for purposes of explanation and not limitation, specific details are set forth, such as particular embodiments, procedures, techniques, etc. in order to provide a thorough understanding of the present invention.

However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The invention claimed is:

1. A handpiece device providing therapeutic and surgical light, comprising:
   a housing including:
      a first haptic feedback element;
      a laser source configured to generate and deliver the therapeutic light and the surgical light from one end of the housing;
      an illumination light source coupled to the housing, configured to generate visible illumination to a user when the handpiece device is in use; and
      a processor, a memory, and a wireless communication means, the processor executing instructions stored in the memory to:
         determine a selection of an operating mode of a plurality of operating modes, the operating mode having a haptic feedback feature;
         receive user input from the user;
         cause the illumination light source to activate in accordance with the operating mode, the operating mode including feedback based on the illumination light source being in one of an off state, an on state, and a state in accordance with a countdown process;
         wirelessly communicate control functions of the device with a display;
         cause the laser source to generate either the therapeutic light or the surgical light;
         and
         cause the first haptic feedback element to generate haptic feedback based on the operating mode.

2. The handpiece device according to claim 1, wherein the first haptic feedback element is located within the handpiece device and the operating mode includes the haptic feedback based on the first haptic feedback element being in one of the off state, the on state, and the state in accordance with the countdown process.

3. The handpiece device according to claim 2, wherein the operating state in accordance with the countdown process is further configured to provide a first haptic feedback, the first haptic feedback having a first intensity at a beginning of the countdown process, the first haptic feedback increasing to a second intensity at the end of the countdown process, the second intensity being greater than the first intensity.

4. The handpiece device according to claim 2, wherein the operating state in accordance with the countdown process is further configured to provide a first haptic feedback, the first haptic feedback having a first vibration at a beginning of the countdown process, the first haptic feedback increasing to a second vibration at the end of the countdown process, the second vibration vibrating at a greater rate than the first vibration.

5. The handpiece device according to claim 2, wherein the operating mode includes generating the therapeutic light for photobiomodulation surgical procedures to soft or hard tissue, ablation, sterilization, and cleaning.

6. The handpiece device according to claim 1, wherein the user input includes a power setting for the therapeutic light received wirelessly by the device.

7. The handpiece device according to claim 6, wherein the processor is configured to selectively and proportionally adjust a magnitude of the haptic feedback based on the power setting.

8. The handpiece device according to claim 1, wherein the illumination light source is associated with a tip of the handpiece device.

9. The handpiece device according to claim 8, wherein the countdown process includes: (a) pulsing the illumination light and a sound indicating a beginning of the countdown process; and (b) pulsing the illumination light and a second sound indicating an end of the countdown process.

10. The handpiece device according to claim 1, wherein the haptic feedback propagates to a tip of the handpiece device, allowing the haptic feedback to be felt by a patient and a sound indicating a state of laser source.

11. The handpiece device according to claim 1, further comprising a foot pedal that is configured to receive the user input to control the therapeutic light.

12. The handpiece device according to claim 11, further comprising a second haptic feedback element is located in the foot pedal, the second haptic feedback element being activated by the processor based on the user input.

13. A device comprising:
   a handpiece that is configured to generate and deliver surgical and therapeutic laser light, the handpiece comprising a first haptic feedback element;
   a foot pedal that is configured to receive input from a user for operating the handpiece, the foot pedal comprising a second haptic feedback element; and
   a processor and a memory, the processor executing instructions stored in the memory to activate the first haptic feedback element and the second haptic feedback element in accordance with a countdown process when the user has selected a surgical or photobiomodulation mode of the device.

14. The device according to claim 13, wherein the foot pedal input includes a power setting for the surgical and therapeutic laser light and the second haptic feedback element being pulsed proportional to the power setting.

15. The device according to claim 14, wherein the processor is configured to selectively and proportionally adjust a magnitude of the haptic feedback produced by the first haptic feedback element or the second haptic feedback element based on the power setting.

16. The device according to claim 13, further comprising an illumination light associated with a tip of the handpiece and visible to the user.

17. The device according to claim 16, wherein the processor is configured to pulse the illumination light and the first haptic feedback element proportional to a power setting.

18. The device according to claim 13, wherein the haptic feedback produced by the first haptic feedback element is propagated to a tip of the handpiece, allowing the haptic feedback to be felt by a patient and a sound indicating a state of laser source.

19. A method comprising:
   determining when a user has selected an operating mode for a handheld device medical laser device;
   receiving input from the user via a handpiece device, a display, or a foot pedal;
   causing a first haptic feedback element in the handpiece device to generate haptic feedback based on the operating mode, the operating mode including providing haptic feedback based on an operating state that includes an off state, an on state, and providing the haptic feedback in accordance with a countdown process;
   enabling a laser source according to the operating mode; and
   starting the countdown process that starts after enabling the laser source.

20. The method according to claim 19, further comprising controlling an illumination light source associated with a tip of the handpiece device in accordance with the operating mode, the operating mode including feedback based on the illumination light source being in one of the off state, the on state, and the state in accordance with the countdown process.

21. The method according to claim 20, wherein the countdown process includes: (a) pulsing the illumination light and a sound indicating a beginning of the countdown process and (b) pulsing the illumination light and a second sound indicating an end of the countdown process.

22. The method according to claim 19, further comprising:
   determining a power setting for a laser light based on the operating mode; and
   selecting a magnitude of the haptic feedback that corresponds to the power setting.

23. The method according to claim 19, further comprising:
   receiving input from the user via the foot pedal; and
   causing a second haptic feedback element in the foot pedal to generate the haptic feedback based on the user input via the foot pedal and the operating mode.

* * * * *

UNITED STATES PATENT AND TRADEMARK OFFICE
CERTIFICATE OF CORRECTION

| | | |
|---|---|---|
| PATENT NO. | : 12,161,405 B2 | Page 1 of 1 |
| APPLICATION NO. | : 17/560911 | |
| DATED | : December 10, 2024 | |
| INVENTOR(S) | : Alexandre B. Di Sessa and Jacob Manshiro Abe | |

It is certified that error appears in the above-identified patent and that said Letters Patent is hereby corrected as shown below:

In the Claims

In Column 10, Line 11, Claim 3, the phrase reciting "operating state" should recite "operating mode."

In Column 10, Line 18, Claim 4, the phrase reciting "operating state" should recite "operating mode."

Signed and Sealed this
Fourth Day of March, 2025

Coke Morgan Stewart
*Acting Director of the United States Patent and Trademark Office*